United States Patent [19]

Tustin

[11] Patent Number: 5,466,832
[45] Date of Patent: Nov. 14, 1995

[54] PROCESS FOR THE MANUFACTURE OF 2,5-DIHYDROFURANS FROM γ,δ-EPOXYBUTENES

[75] Inventor: Gerald C. Tustin, Kingsport, Tenn.

[73] Assignee: Eastman Chemical Company, Kingsport, Tenn.

[21] Appl. No.: 388,004

[22] Filed: Feb. 13, 1995

[51] Int. Cl.⁶ .................... C07D 307/28; C07D 493/00
[52] U.S. Cl. ............................................. 549/330; 549/507
[58] Field of Search ...................................... 549/507, 330

[56] References Cited

U.S. PATENT DOCUMENTS

| | | | |
|---|---|---|---|
| 5,081,096 | 1/1992 | Monnier et al. | 502/348 |
| 5,082,956 | 1/1992 | Monnier et al. | 549/507 |
| 5,238,889 | 8/1993 | Falling et al. | 549/507 |
| 5,315,019 | 5/1994 | Phillips et al. | 549/507 |

Primary Examiner—C. Warren Ivy
Assistant Examiner—Amelia Owens
Attorney, Agent, or Firm—J. Frederick Thomsen; Harry J. Gwinnell

[57] ABSTRACT

Disclosed is a process for the preparation of 2,5-dihydrofurans by the homogeneous, liquid phase isomerization of γ,δ-epoxyalkene compounds wherein a γ,δ-epoxyalkene compound is isomerized in an inert, organic solvent containing a catalytic amount of a soluble copper salt. The process is particularly useful for the conversion of 3,4-epoxy-1-butene to 2,5-dihydrofuran.

8 Claims, No Drawings

PROCESS FOR THE MANUFACTURE OF 2,5-DIHYDROFURANS FROM γ, δ-EPOXYBUTENES

This invention pertains to the preparation of 2,5-dihydrofurans by the homogeneous, liquid phase isomerization of γ,δ-epoxyalkene compounds. More specifically, this invention pertains to the isomerization of γ,δ-epoxyalkene compounds in an inert, organic solvent utilizing a catalytic amount of a soluble copper salt.

2,5-Dihydrofuran compounds are useful intermediates for the production of a wide variety of industrial and fine chemicals. For example, 2,5-dihydrofuran is an starting material for the production of the two important industrial chemicals, tetrahydrofuran and 1,4-butanediol. Tetrahydrofuran is a useful solvent and precursor to poly(tetramethylene glycol) (PTMG). Tetrahydrofuran can be produced by the hydrogenation of 2,5-di-hydrofuran. 1,4-Butanediol is an important monomer for a variety of polyesters and polyurethanes. It also can be converted to tetrahydrofuran by dehydration. 1,4-Butanediol can be produced from 2,5-dihydrofuran by rearrangement to 2,3-dihydrofuran followed by hydration and hydrogenation.

2,5-Dihydrofuran compounds may be obtained by the rearrangement of γ,δ-epoxyalkene compounds such as 3,4-epoxy-1-butene. The γ,δ-epoxyalkene compounds can readily be prepared by the vapor phase oxidation of substituted and unsubstituted 1,3-butadienes. Other potential rearrangement products of 3,4-epoxy-1-butene include both isomers of crotonaldehyde, unstable 3-butenal, 3-buten-2-one, 2,3-dihydrofuran and others. A need exists for an efficient process that will rearrange γ,δ-epoxyalkene compounds to 2,5-dihydrofurans with minimal production of the other rearrangement products.

In *Can. J. Chem.* 54, 3364–3376 (1976), Crawford, Lutener and Cockcroft teach that thermolysis of 3,4-epoxy-1-butene in the absence of catalysts produces a mixture of crotonaldehydes (the most abundant product) and about equal amounts of 3-butenal and 2,3-dihydrofuran. Extended thermolysis produces carbon monoxide and propylene as the most abundant products. No 2,5-dihydrofuran is produced by this treatment.

In *J. Organomet. Chem.* 359, 255–266 (1989), Sato, Matsuda and Izumi teach that rhodium (I) compounds catalyze the isomerization of 3,4-epoxy-1-butene to crotonaldehyde. In *J. Amer. Chem. Soc.* 101, 1623–1625 (1979), Suzuki, Oda and Noyori teach that diene epoxides isomerize to unsaturated carbonyl compounds in the presence of palladium (0). Thus, the prior art suggests to those skilled in the art that low valent transition metals would not be effective catalysts for the isomerization of γ,δ-epoxyalkene compounds, such as 3,4-epoxy-1-butene, to 2,5-dihydrofuran compounds.

Several examples of the use of iodide ion as a catalyst for the conversion of 3,4-epoxy-1-butene to 2,5-dihydrofuran have appeared in the prior art. In the processes disclosed in U.S. Pat. Nos. 3,932,468 and 3,996,248, hydrogen iodide catalyzes the isomerization in amide solvents. This process suffers from the use of the corrosive hydrogen iodide. Improved iodide-catalyzed processes are described in U.S. Pat. Nos. 5,082,956 and 5,315,019 whereby the use of hydrogen iodide is avoided by the use of Lewis acids, such as organo-tin iodide compounds, in combination with quaternary phosphonium or ammonium iodide salts. The process of U.S. Pat. Nos. 5,082,956 and 5,315,019 produces iodine-containing organic byproducts and consumes expensive iodine. Thus, a need exists for a process that will catalyze the rearrangement of γ,δ-epoxyalkene compounds to 2,5-dihydrofuran compounds and avoids the use of iodine-containing materials.

I have discovered that γ,δ-epoxyalkene compounds may be isomerized to the corresponding 2,5-dihydrofuran compounds by an iodine-free process wherein the former is contacted with a solution of a copper salt in an inert, organic solvent. The present invention therefore provides a process for the preparation of a 2,5-dihydrofuran compound which comprises contacting at elevated temperature a γ,δ-epoxyalkene compound with a catalytic amount of a copper salt dissolved in an inert, organic solvent. The 2,5-dihydrofuran isomerization product may be recovered from the reaction mixture by conventional distillation techniques.

The soluble copper salt used as the catalyst in the present invention may be selected from both copper (I) and copper (II) salts although copper (I) salts are preferred. The copper salt catalysts preferably are selected from the chlorides and bromides of copper (I) and copper (II) with cuprous chloride being particularly preferred. The molar ratio of the γ,δ-epoxyalkene reactant to copper salt catalyst may span from a low of about 1:1 to a high of about 1000:1. The preferred molar ratio of γ,δ-epoxyalkene reactant to copper salt catalyst is about 10:1 to 1:1. Higher amounts of catalysts provide higher rates, but 90% conversion can be achieved in one hour when the γ,δ-epoxyalkene to copper salt molar ratio is 10:1. Lower amounts of catalyst provide lower rates but provide better utilization of the catalyst, i.e., more product is produced per mole of catalyst.

The process of this invention is carried out in the presence of an inert, organic solvent in which both the γ,δ-epoxyalkene reactant and copper salt catalyst are soluble. The inert, organic solvent may be selected from aliphatic, cycloaliphatic and aromatic hydrocarbons, including alkyl-substituted aromatic hydrocarbons, containing from 6 to about 18 carbon atoms; N,N-disubstituted carboxylic acid amides containing a total of 3 to 8 carbon atoms; and aliphatic, cycloaliphatic and aromatic nitriles containing up to about 10 carbon atoms. The organonitriles, especially the aromatic nitriles containing 6 to 10 carbon atoms, are the preferred solvents. Benzonitrile is an excellent solvent for the reaction, although substituted benzonitriles, such as p-methoxybenzonitrile or p-chlorobenzonitrile, or mixtures thereof may be used as solvents as well. The weight ratio of the inert, organic solvent to γ,δ-epoxyalkene reactant may vary substantially depending on various factors such as the particular copper salt, γ,δ-epoxyalkene reactant, and solvent being used. Normally, the solvent:reactant weight ratio will be in the range of about 0.1:1 to 10:1. The preferred weight ratio is in the range of about 1.5:1 to 7:1. Excessive dilution of the mixture with solvent adversely affects the rate of isomerization.

Although not essential, the inclusion of certain phosphorous-containing ligands has a favorable effect on isomerization rate. The preferred phosphorous-containing ligands are organophosphites such as tri-alkylphosphites, tricycloalkylphosphites and triarylphosphites wherein the alkyl groups contain 1 to 6 carbon atoms, the cycloalkyl groups contain 5 to 10 carbon atoms, and the aryl groups contain 6 to 10 carbon atoms. Triphenyl phosphite is a preferred phosphorous-containing ligand. The amount of phosphorous-containing ligand which may be used typically will be in the range of about 0.1 to 4 moles ligand per mole of copper salt. The preferred phosphorus ligand:copper salt molar ratio ranges from about 0.5:1 to 2:1.

As noted above, the process of the present invention is carried out at elevated temperatures, e.g., temperatures in the range of about 80° C. to 250° C. The process preferably is operated at a temperature in the range of 110° to 220° C., and most preferably at a temperature in the range of 150° to 200° C. Rates are slow at the lower temperature extreme, and byproduct formation is excessive at higher temperatures.

The process of the invention preferably is performed at greater than one atmosphere pressure, although satisfactory results can be obtained by refluxing the homogeneous. liquid mixtures at one atmosphere. The reaction preferably is performed in a sealed vessel, such as an autoclave, capable of withstanding greater than one atmosphere pressure. Normally, the process is carried out in the presence of or under an inert gas, such as nitrogen, to prevent unwanted oxidation reactions. When an inert gas is used, it may be vented from the autoclave before the heating is begun or it may be retained at a pressure greater than one atmosphere. Two hundred psig is a satisfactory pressure to maintain the inert gas before heating. Higher pressures may be used if desired, but no benefits result from use of excessively high pressure. Generally the reaction mixture is agitated by stirring or rocking. The reaction can be performed as a batch or a continuous process.

The γ,δ-epoxyalkene reactants may contain from 4 to about 8 carbon atoms. Examples of the epoxyalkene and epoxycycloalkene reactants include compounds having the structural formula:

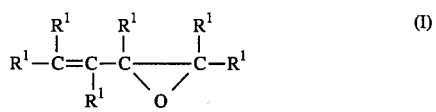

wherein each $R^1$ is independently selected from hydrogen and methyl or 2 $R^1$ substituents collectively may represent an alkylene radical which with the carbon atoms to which they are attached forms a cycloalkene group having about 5 to 8 carbon atoms. The preferred epoxyalkene reactants comprise compounds of formula (I) wherein a maximum of four of the $R^1$ substituents individually may represent methyl. Exemplary compounds contemplated for use in the practice of the present invention include 3,4-epoxy-3-methyl-1-butene, 3,4-epoxy-2-methyl-1-butene, 2,3-dimethyl-3,4-epoxy-1-butene, 3,4-epoxy-1-butene, 2,5-dimethyl-2,4-hexadiene monoepoxide, 3,4-epoxycyclooctene and the like. The epoxyalkene reactant of primary interest is 3,4-epoxy-1-butene.

The 2,5-dihydrofuran compounds obtained in accordance with our novel process have the structural formula:

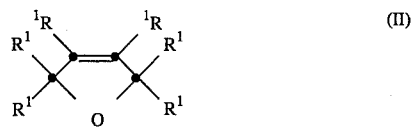

wherein the $R^1$ substituents are defined above. Of the compounds which may be obtained in accordance with our invention, the most important is 2,5-dihydrofuran.

The 2,5-dihydrofuran product can be isolated from the reaction mixture by distillation. Isolation of the 2,5-dihydrofuran product (B.P. 66°–67° C.) by distillation is facilitated if all of the 3,4-epoxy- 1-butene (B.P. 65°–66° C.) has been converted. Byproduct crotonaldehyde (B.P. 104° C.), a starting material for the manufacture of butanol and butyraldehyde, is produced in lower amounts than the 2,5-dihydrofuran by the preferred conditions of the invention and also may be isolated from the reaction mixture by distillation. Benzonitrile solvent (B.P. 188° C.) also may be recovered by distillation, or more 3,4-epoxy-1-butene may be added to the copper-containing, undistilled benzonitrile solvent and the process of the invention repeated. If desired, copper may be recovered from the liquid product mixture by extraction, for example, with aqueous ammonium hydroxide. If desired, distillation residues may be destroyed by oxidation, and copper residues may be extracted from the oxidized products. Combinations of the above-described purification schemes are also within the scope of the invention. Other purification schemes known to those skilled in the art are within the scope of the invention.

The process of the present invention is further illustrated by the following examples.

EXAMPLE 1

This example illustrates the process of the invention without the use of a phosphorous-containing ligand. A mixture of 14.0 g 3,4-epoxy-1-butene, 50 g benzonitrile and 2.0 g cuprous chloride were charged into a 300 mL, stainless steel, rocking autoclave. The autoclave was pressurized to 200 psig with nitrogen and the nitrogen was then released. The nitrogen pressurization and releasing procedure was repeated two more times. The autoclave was again charged with 200 psig nitrogen, sealed and then heated to 150° C. with rocking agitation at autogenous pressure. Heating with rocking agitation was continued for four hours at autogenous pressure. The autoclave then was cooled to room temperature and then vented. The liquid product was weighed and analyzed for weight percent of volatile products by gas chromatography. The product contained 4.1 g 2,5-dihydrofuran and 0.8 g crotonaldehyde.

EXAMPLE 2

This example illustrates the use of a phosphorous-containing ligand under conditions of low catalyst concentration. The procedure of Example 1 was repeated with 28.0 g 3,4-epoxy-1-butene, 50 g benzonitrile, 0.05 g cuprous chloride and 0.32 g triphenyl phosphite charged to the autoclave. The product contained 2.9 g 2,5-dihydrofuran and 0.6 g crotonaldehyde. Each equivalent of copper catalyst produced 82 equivalents of 2,5-dihydrofuran.

EXAMPLE 3

This example illustrates the use of a phosphorous-containing ligand under conditions of higher catalyst concentration and different ligand:copper salt mole ratio than in Example 2. The procedure of Example 2 was repeated with 0.5 g cuprous chloride instead of 0.05 g and 1.57 g triphenyl phosphite instead of 0.32 g. The product contained 6.0 g 2,5-dihydrofuran and 0.02 g crotonaldehyde.

EXAMPLE 4

This example illustrates the effects of elevated temperature on the process of the invention without the use of a phosphorous-containing ligand and an intermediate amount of catalyst. The procedure of Example 1 was performed using 0.5 g cuprous chloride at 200° C. instead of 150° C. The product contained 4.9 g 2,5-dihydrofuran and 0.2 g crotonaldehyde.

EXAMPLE 5

This example illustrates the effect of changing the solvent to acetonitrile. The process of Example 1 was performed replacing the benzonitrile with 50 g acetonitrile. The product contained 4.1 g 2,5-dihydrofuran and 2.1 g crotonaldehyde.

EXAMPLE 6

This example illustrates the effect of changing the solvent to p-xylene. The process of Example 1 was repeated replacing the benzonitrile with 50 g p-xylene. The product contained 0.2 g 2,5-dihydrofuran and 0.5 g crotonaldehyde.

EXAMPLE 7

This example illustrates the effect of changing the solvent to hexane. The process of Example 1 was repeated replacing the benzonitrile with 50 g hexane. The product contained 0.1 g 2,5-dihydrofuran and 0.4 g crotonaldehyde.

EXAMPLE 8

This example illustrates the combined effects of reducing the reaction temperature, the catalyst loading and the reaction time. The process of Example 5 was performed at 130° C. instead of 150° C. using 1.25 g cuprous chloride instead of 2 g and heated for 2.5 hours instead of 4 hours. The product contained 0.8 g 2,5-dihydrofuran and 0.6 g crotonaldehyde.

EXAMPLE 9

This example illustrates the effect of changing the catalyst to cuprous bromide. The process of Example 8 was performed using 1.81 g cuprous bromide in place of cuprous chloride. The product contained 0.7 g 2,5-dihydrofuran and 0.8 g crotonaldehyde.

EXAMPLE 10

This example illustrates the effect of changing the catalyst to cupric chloride. The process of Example 8 was performed using 1.69 g anhydrous cupric chloride. The product contained 0.6 g 2,5-dihydrofuran and 3.5 g crotonaldehyde.

The invention has been described in detail with particular reference to preferred embodiments thereof, but it will be understood that variations and modifications can be effected within the spirit and scope of the invention.

I claim:

1. Process for the preparation of a 2,5-dihydrofuran compound which comprises contacting at elevated temperature a γ,δ-epoxyalkene compound with a catalytic amount of a copper salt dissolved in an inert, organic solvent.

2. Process according to claim 1 wherein the elevated temperature is in the range of about 110° to 220° C. the 2,5-dihydrofuran compound has the formula

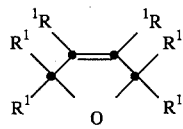
(II)

and the γ,δ-epoxyalkene compound has the formula

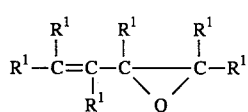
(I)

wherein each $R^1$ is independently selected from hydrogen and methyl or 2 $R^1$ substituents collectively may represent an alkylene radical which with the carbon atoms to which they are attached forms a cycloalkene group having about 5 to 8 carbon atoms.

3. Process according to claim 2 wherein the copper salts is selected from the chlorides and bromides of copper (I) and copper (II).

4. Process for the preparation of 2,5-dihydrofuran which comprises contacting 3,4-epoxy-1-butene at a temperature of about 110° to 220° C. with a catalytic amount of a copper (I) chloride or bromide dissolved in an inert, organic solvent.

5. Process according to claim 4 wherein the process is carried out in the presence of an organophosphite ligand selected from trialkylphosphites, tricycloalkylphosphites and triarylphosphites wherein the alkyl groups contain 1 to 6 carbon atoms, the cycloalkyl groups contain 5 to 10 carbon atoms, and the aryl groups contain 6 to 10 carbon atoms; and the inert, organic solvent is selected from aliphatic, cycloaliphatic and aromatic hydrocarbons containing from 6 to about 18 carbon atoms; N,N-disubstituted carboxylic acid amides containing a total of 3 to 8 carbon atoms; and aliphatic, cycloaliphatic and aromatic nitriles containing up to about 10 carbon atoms.

6. Process for the preparation of 2,5-dihydrofuran which comprises contacting 3,4-epoxy-1-butene at a temperature of about 110° to 220° C. with a catalytic amount of a copper(I) chloride or bromide dissolved in an inert, organic solvent selected from aliphatic, cycloaliphatic and aromatic nitriles containing up to about 10 carbon atoms; in the presence of a an organophosphite ligand selected from trialkylphosphites, tricycloalkylphosphites and triarylphosphites wherein the alkyl groups contain 1 to 6 carbon atoms, the cycloalkyl groups contain 5 to 10 carbon atoms, and the aryl groups contain 6 to 10 carbon atoms wherein the molar ratio of the ligand to copper(I) chloride or bromide is about 0.1:1 to 4:1.

7. Process according to claim 6 for the preparation of 2,5-dihydrofuran which comprises contacting 3,4-epoxy-1-butene at a temperature of about 150° to 200° C. with a catalytic amount of cuprous chloride dissolved in an inert, organic solvent selected from aliphatic, cycloaliphatic and aromatic nitriles containing up to about 10 carbon atoms; in the presence of a an organophosphite ligand selected from trialkylphosphites, tricycloalkylphosphites and triarylphosphites wherein the alkyl groups contain 1 to 6 carbon atoms, the cycloalkyl groups contain 5 to 10 carbon atoms, and the aryl groups contain 6 to 10 carbon atoms wherein the molar ratio of the ligand to copper(I) chloride or bromide is about 0.5:1 to 2:1.

8. Process according to claim 7 wherein the inert, organic solvent is benzonitrile and the organophosphite ligand is triphenylphosphite.

* * * * *